(12) United States Patent
Fleischmann (10) Patent No.: US 6,432,398 B1
(45) Date of Patent: Aug. 13, 2002

(54) METHODS OF TREATING DISEASED CELLS

(76) Inventor: W. Robert Fleischmann, 21 Manor Way, Galveston, TX (US) 77550

( * ) Notice: Subject to any disclaimer, the term of this patent is extended or adjusted under 35 U.S.C. 154(b) by 0 days.

(21) Appl. No.: 09/786,872

(22) PCT Filed: Sep. 16, 1999

(86) PCT No.: PCT/US99/21282

§ 371 (c)(1),
(2), (4) Date: Mar. 9, 2001

(87) PCT Pub. No.: WO00/18427

PCT Pub. Date: Apr. 6, 2000

Related U.S. Application Data (60) Provisional application No. 60/102,386, filed on Sep. 29, 1998.

(51) Int. Cl.[7] .............................................. A61K 38/21
(52) U.S. Cl. ..................................................... 424/85.4
(58) Field of Search ........................................ 424/85.4

(56) References Cited

U.S. PATENT DOCUMENTS

| | | | | |
|---|---|---|---|---|
| 5,028,422 A | * | 7/1991 | Tanner et al. | 424/85.4 |
| 5,236,707 A | * | 8/1993 | Stewart, II | 424/85.7 |
| 5,372,808 A | * | 12/1994 | Blatt et al. | 424/85.4 |

* cited by examiner

*Primary Examiner*—Raymond Henley, III
(74) *Attorney, Agent, or Firm*—Robert D. Fish; Rutan & Tucker (57) ABSTRACT

Diseased cells are removed from a patient or other system, contacted with an interferon for at least 48 hours, and reintroduced into the system. In preferred methods the diseased cells are afflicted with a cancer, a bacterium, a fungus, or a virus, and the interferon is an alpha-interferon. The diseased cells are contacted with the interferon for a relatively long period of time, such as 2, 5, 7, 14 days, or even longer, and at least partially inactivated before being reintroduced.

18 Claims, 3 Drawing Sheets

Figure 1. Vaccination of C57Bl/6 mice with uvB16α cells. Mice were vaccinated i.p. on days -21, -14, -7, and 0 with $10^6$ uvB16a cells or mock vaccinated. The uvB16 α cells were pretreated for >14 days with the indicated concentrations of IFN- α. On day 0, the mice were challenged i.p. with $10^6$ live B16 cells. Day of death was noted. The graph plots the combined data of two experiments as cumulative survival versus day after tumor inoculation.

FIGURE 1

Figure 2. Vaccination of C57Bl/6 mice with inactivated B16 or B16αcells. To determine the effect of vaccination dosage, mice were inoculated i.p. on days −21, −14, −7, and 0 with $10^4$ (Panel A), $10^5$ (Panel B), or $10^6$ (Panel F) UV-irradiated B16α cells. On day 0, the mice were challenged i.p. with $10^7$ live B16 cells. To determine the effect of number of vaccinations, mice were inoculated i.p. two times (Panel C), three times (Panel D), or four times (Panel F) at weekly intervals with wither $10^6$ UV-irradiated B16 or UV-irradiated B16α cells. On day 0, the mice were challenged i.p. with $10^7$ live B16 cells. To determine the potency of the vaccination procedure, mice were inoculated i.p. on days −21, −14, −7, and 0 with either $10^6$ UV-irradiated B16 or UV-irradiated B16α cells. On day 0, mice were challenged i.p. with $10^6$ (Panel E) or $10^7$ (Panel F) live B16 cells. Control mice were all mock inoculated with the carrier (HBSS). Day of death was noted. The graphs plot the combined data of two experiments as cumulative survival vs. day after tumor inoculation. Open squares, control; open circles, UV-irradiated B16 vaccination; closed circles, UV-irradiated B16α vaccination.

FIGURE 2

Figure 1. Western blots of B16 and B16α membrane surface proteins. Equal amounts (25μg) of purified membrane proteins from B16 and B16α cells were subjected to SDS-PAGE. Proteins from the gel were then blotted onto a nitrocellulose membrane by semi-dry electrophoretic transfer. The blot was incubated with pooled antisera from mice that had been vaccinated 4 times with irradiated B16 cells (Panel a) or with irradiated B16α cells (Panel b). Lane (1) represents bands of standard molecular weight markers (A= 203 kDa, B = 115 kDa, C=83 kDa, and D=49.4 kDa). Lane (2) represents bands of antiserum-recognized parental B16 membrane proteins. Lane (3) represents bands of antiserum-recognized B16α membrane proteins. Band X1 (100 kDa), X2 (80 kDa), and X3 (44.5 kDa) represent surface antigens recognized by one or both of the antibody preparations.

FIGURE 3

METHODS OF TREATING DISEASED CELLS

This is a 371 of PCT/US99/21282 filed Sep. 16, 1999 which claims the benefit of U.S. Provisional Application No. 60/102,386 filed Sep. 29, 1998.

FIELD OF THE INVENTION

The field of the invention is treatment of diseased cells.

BACKGROUND OF THE INVENTION

Today, progress has been made against many diseases, including cancers, bacterial and viral infections. In the case of cancers, for example, surgery, chemotherapy, radiation, and cytokine therapies have all made significant contributions in either curing the conditions, or at least prolonging the lives of the patients. Similarly, antibiotics have made significant inroads against bacterial infections, and even viral infections have been successfully treated with various compounds such as ribavirin and interferon. Despite all of these advancements, however, there continues to be a need for more effective treatments.

One promising avenue is the use of cytokines. Cytokines are relatively small molecules having broad antiviral, antiproliferative and immunomodulatory effects. One particular class of cytokines, the interferons (IFN), are especially interesting, having been recognized as providing antiproliferative activities, as well as for antiviral and immunoregulatory activities (Fleishman, C M et al., "Differential Antiproliferative Activities of IFNs α, β and γ: Kinetics of Establishment of Their Antiproliferative Effects and The Rapid Development of Resistance to IFNs α and β", *J. Bio. Regulators and Homeostatic Agents*, 1988, Vol. 2, no. 4, pp 173–185). In the field of cancer, for example, studies have concluded that in vivo administration of interferons have some efficacy for a number of neoplastic conditions, including hairy cell leukemia, Kaposi's sarcoma in AIDS, chronic granulomatous disease, chronic myelogenous leukemia, non-Hodgkin's lymphoma, multiple myeoloma, cutaneous T cell lymphoma, malignant melanoma, renal cell carcinoma, carcinoid, and cervical intraephithelial neoplasia. Unfortunately, in vivo administration of cytokines is generally less efficacious with respect to treating most cancers as cytotoxic drugs, radiation, and chemotherapy. In addition, in vivo use of cytokines (i.e. intravenous or other direct administration) has detrimental side effects.

Ex vivo use of cytokines has also been studied, and some researchers have achieved moderately promising results with ex vivo treatment using IL-2 (see e.g., Steven Rosenberg's work). On the other hand, ex vivo treatment of diseased cells with IFN has not been effective, and work in this area has more or less been terminated.

In hindsight, such failure should have been expected. With respect to short-term exposures, studies show that subjecting cells to interferon for 24 hours or less does not stimulate presentation of surface antigens. Since antigen presentation is generally needed to trigger an effective immune response, it follows that such treatment would provoke little or no immune response. With respect to long-term exposure, it is generally recognized that interferon treatment inhibits the growth of cells, and as such one would expect that tumor cells would not be able to be cultured long term in the presence of interferon. Still further, it is known that cells harvested from an organism rapidly accommodate to their ex vivo environment, and tend to present antigens that are ever more modified as compared with antigens produced by similar cells remaining in vivo. Therefore, one of ordinary skill in the art would conclude that long-term ex vivo exposure of cells to interferon would be detrimental to the overall effectiveness of this treatment. Even further, there is no teaching or suggestion for long-term exposure of cells to interferon.

Thus, there is still a need to provide methods by which cytokines in general, and interferons in particular, can be employed in the ex vivo treatment of diseased cells.

SUMMARY OF THE INVENTION

The present invention provides methods for treating diseased cells in a system, and generally comprises removing a sample of the diseased cells from the system, contacting the diseased cells with an interferon for at least 48 hours, and reintroducing the interferon contacted cells into the system.

In one aspect of preferred embodiments, the system is a vertebrate, preferably a human. But it could also be used to treat cancers in pets such as dogs or cats, or other valued animals. In another aspect of preferred embodiments, the diseased cells are afflicted with a cancer, a bacterium, a virus or a fungus. In still other aspects of preferred embodiments, the interferon is a Type 1 interferon, i.e., interferon alpha, interferon beta, interferon tau, interferon omega, or a genetically created recombinant form of interferon such as consensus alpha. In still other aspects of preferred embodiments, the diseased cells are placed in contact with the interferon (or interferons) for a relatively long period of time, such as 36 hours, 48 hours, 72 hours, 5 days, 7 days, 10 days, 14 days, or even longer. In still other aspects of preferred embodiments, the cells reintroduced into the system are at least partially inactivated. In still other aspects of preferred embodiments, the cells can be reintroduced into a system which is at particularly high risk for a given disease, and in that sense act as a vaccine.

Various objects, features, aspects and advantages of the present invention will become more apparent from the following detailed description of preferred embodiments of the invention.

DETAILED DESCRIPTION

A preferred method of using an interferon to treat a patient having diseased cells generally comprises removing the diseased cells (10), treating the diseased cells with an interferon (20), optionally deactivating the treated cells (30), and reintroduction of the treated cells into the patient (40).

The patient is contemplated to be any higher organism having diseased cells present in its body at the time of the treatment. Contemplated patients include vertebrates, especially mammals, and most especially humans. Treatment of livestock, and pets such as cats and dogs, are also of particular interest.

Diseased cells are contemplated to any cells of which the patient wants to eliminate. Contemplated diseased cells include afflicted with a disease of genetic lesion, viral, bacterial, mycotic, chemical, or structural derivation. Where the disease comprises a cancer, particularly preferred embodiments are directed to at least one of a melanoma, a breast cancer, a liver cancer, and a prostate cancer.

Diseased cells may be removed from a patient through any suitable harvesting procedure whereby the diseased cells are physically collected from the body of the patient. Such harvesting procedures, for example, include scraping, resection, aspiration, or any other means of biopsy or surgical or non-surgical removal.

Either a section of a diseased cell mass, or the entire diseased cell mass may be removed. In some cases, only a portion of the diseased cell area may need to be removed to effect treatment on the entire diseased cell area. In other cases, most or all of the diseased area may need to be removed in order to effectively treat the patient.

It is contemplated that diseased cells can be removed from anywhere on the patient's body depending on the location of the diseased cell. Contemplated areas of the patient's body which are available for cell harvesting include the brain, skin, bone marrow, reproductive organs, breast, thyroid, lung, kidney, adrenals, pancreas, intestine, bladder, stomach and liver.

The amount of diseased cells required for treatment may vary. It is contemplated that up to $10^6$ to $10^7$ cells or more are required for per treatment for treatment to be effective.

Diseased cells may either be confined to the targeted mass harvested from the patient, or combined with diseased or non-diseased cells from another source. Such other sources could be cell libraries, other patients, or another location on the patient. It is contemplated that cells from other sources may need to be combined with patient's own diseased cells in the case where there are not enough of patient's own harvested cells to effect treatment, where patient's own diseased cells are not stable enough to survive outside of the body without support from other cell matrices, or any other time whereby patient's own cells are not adequate to effect proper treatment.

Cells which are provided may be placed in a receiving apparatus, such as a plastic culture dish, wherein the cells may be stored, modified or manipulated in any other suitable manner.

Cells may be maintained in a suitable medium, such as a growth medium or saline solution, which may be supplemented with other solutions as required, such as fetal bovine serum, sodium bicarbonate, penicillin or streptomycin.

Cell lines, which are described herein to mean any contained collection of cells maintained under similar conditions, may be stored in any apparatus suitable for the maintenance of the cell lines, such as an incubator, chemostat or other growth chamber, refrigerator, freezer or other cold storage chamber, or as a lyophilized preparation. Thus, it is contemplated that one might be able to therapeutically administer dead whole cells, or lyophilized and reconstituted cells.

Cells may be subjected to growth inhibitors, such as physical, chemical or biological stressors, such as interferons and other cytokines and lymphokines, freezing, enucleation, anti-neoplastic drugs.

Interferons are contemplated to be any natural body proteins that exhibit antiproliferative activities, as well as antiviral and immunoregulatory activities. Such interferons are contemplated to comprise interferon-$\alpha$, interferon-$\beta$, and any other suitable interferon. A preferred embodiment may be to use recombinant human interferon-$\alpha$, or rHu-IFN-$\alpha$A/D in non-human animals.

Cell lines may be supplemented with different concentrations of interferon. Such concentrations range from 0–10,000 U/ml of interferon or more as contemplated. Preferred concentrations of interferon are 1,000 U/ml; 3,000 U/ml; and 5,000 U/ml with 3,000 U/ml being the most preferred concentration.

Cell lines may be stored in combination with interferon for a short time ($\leq$24 hours) or a long time (>24 hours) as contemplated. A preferred embodiment is to store the cell lines in interferon for 14 days.

Cells may be optionally inactivated by using some method, such as irradiation by UV light or gamma radiation, enucleation, or anti-neoplastic drugs. A preferred embodiment is to use irradiation to deactivate cells.

Deactivated cells may be washed, centrifuged and re-suspended as required by the parameters of the treatment. A preferred method comprises washing the cells three times with Hank's balanced salt solution (HBSS), removed from the storing apparatus (by incubating with EDTA for attached cells), washed a second time with HBSS, centrifuged and re-suspended in HBSS.

Treated cells are defined herein as those cells which are reacted with interferon and either deactivated, left active, or are a combination thereof.

Treated cells may be collected by suitable collection means, such as centrifugation or other methods of precipitation of the cells, and introduced into the patient by a suitable method, such as injection.

Treated cells may be reintroduced into the patient at appropriate time intervals, such as every 7–10 days. A preferred method is to introduce treated cells into the patient once a week for 2 to 6 weeks, with periodic boosters as needed. Need can be established by monitoring one or more appropriate parameters related to the disease, such as PSA, such as carcino-embryonic antigen, and so forth. Cells are contemplated to be reintroduced by any suitable mechanism, including especially by injecting the cells into the system subcutaneously, intraperitoneally, or intravenously.

It is also contemplated that cells subjected to long-term incubation in interferon can be reintroduced into a system that is at particularly high risk for a given disease, and in that sense act as a vaccine. Thus, for example, patients expressing the Br1 breast cancer gene, patients having high serum levels of the prostate antigen (PAS).

EXAMPLES

Mice: Pathogen-free female C57B1/6 mice were obtained from The Jackson Laboratory (Bar Harbor, Me.). The mice were provided with sterilized food and bedding, housed in front of animal isolators in a virus-free animal facility, and used between 8 to 12 weeks of age. The pathogen-free condition of the mice was routinely confirmed by antibody testing.

Tumor cells: Murine B16-F1 melanoma cells (B16 cells) obtained from Dr. I. Fidler (Fidler, I J, "Selection of successive tumor lines for metastasis", Nature, 1973, *Nature New Biol.,* 242, 148–159) were maintained in 100-mm and 150-mm plastic culture dishes (Corning Glass Works, Corning, N.Y.) in a growth medium of EMEM (Earle's base, Gibco, Grand Island, N.Y.) supplemented with 10% fetal bovine serum (FBS, Intergen, Purchase, N.Y.), 0.22% sodium bicarbonate, penicillin (100 U/ml, Pfizer, New York, N.Y.), streptomycin (100 µg/ml, Pfizer), and gentamicin (11 µg/ml, Invernex, Chagrin Falls, Ohio). In vitro IFN-$\alpha$-treated B16-F1 melanoma cells (B16$\alpha$ cells) were cultured as described above in medium supplemented with 300, 1,000, 3,000, or 10,000 U/ml of rHuIFN-$\alpha$A/D for at least 2 weeks before inoculation into mice. B16-F10 melanoma cells, also obtained from Dr. I. Fidler, were maintained as described above in EMEM supplemented with 5% fetal bovine serum, 0.22% sodium bicarbonate, penicillin (100 U/ml), streptomycin (100 μg/ml), gentamicin (11 μg/ml), 2% 100X vitamins (Gibco, Grand Island, N.Y.), 1% 2 mM L-glutamine (Sigma, St. Louis, Mo.), 1% 100 mM sodium puruvate (Sigma, St. Louis, Mo.), and 1% 100X non-essential amino acids (Gibco, Grand Island, N.Y.). All cell lines were maintained in a humidified incubator at 37° C. with 5% $CO_2$ and passaged two times weekly.

Interferon: Purified recombinant human IFN-α, rHuIFN-αA/D (IFN-α), was generously provided by Dr. Michael Brunda (Hoffman-LaRoche, Nutley, N.J.) and had a specific activity of $6.5 \times 10^7$ U/mg protein. This interferon can cross species barriers and has been shown to be as effective in the murine system as murine IFN-α and IFN-β.

In vivo tumor models: B16 variant cell monolayers were detached by incubation with 2 mM EDTA (Sigma, St. Louis, Mo.) in PBS at 37° C. for 5 min. The detached cells were washed once with HBSS, centrifuged, and resuspended in fresh culture medium. Mice were inoculated i.p. into the right mid-abdominal region with a B16 innoculum of $10^6$ or $10^7$ cells/0.1 ml; s.c. on the right mid-abdominal region with a B16 innoculum of $10^5$ cells/0.1 ml; or i.v. into a lateral tail vein in the mid-tail region with a B16-F10 innoculum of $5 \times 10^5$ cells/0.05 ml. For the i.p.- and the s.c.-inoculated solid tumor models, the day of death was monitored for each mouse. For the i.v.-inoculated metastatic tumor model, metastases in the lungs were quantitated by blind enumeration of the darkly pigmented modules at 16 days after inoculation.

Vaccination protocols: All vaccinations were performed in the absence of any adjuvant. B16 or B16α cells were UV-inactivated by 17 min exposure to $4 \text{ erg} \times \sec^{-1} \times m^{-2}$, washed 3 times with HBSS, removed from the dishes by incubating with 2 mM EDTA in PBS at 37° C. for 5 min, washed one more time with HBSS, centrifuged, resuspended in HBSS, and counted. For the i.p. and the i.v. challenge models described above, UV-inactivated cells were inoculated i.p. once a week for two, three, or four weeks. Live B16 or B16-F10 cells were inoculated immediately following the last inoculation of inactivated cells. For the s.c. challenge model, UV-inactivated cells were inoculated, beginning 3 days after the challenge, either i.p. or s.c. once a day for 4 days followed by 2 additional weekly inoculations (for a total of 6 vaccinations). Control mice received mock vaccinations with carrier (HBSS) and were also challenged on the same day as the test mice. Percent Increase in Life Span was calculated for the vaccinated mice as the following: (Day of death for a vaccinated mouse—Average day of death for control mice)×100%=Average day of death for control mice.

Figure 1:
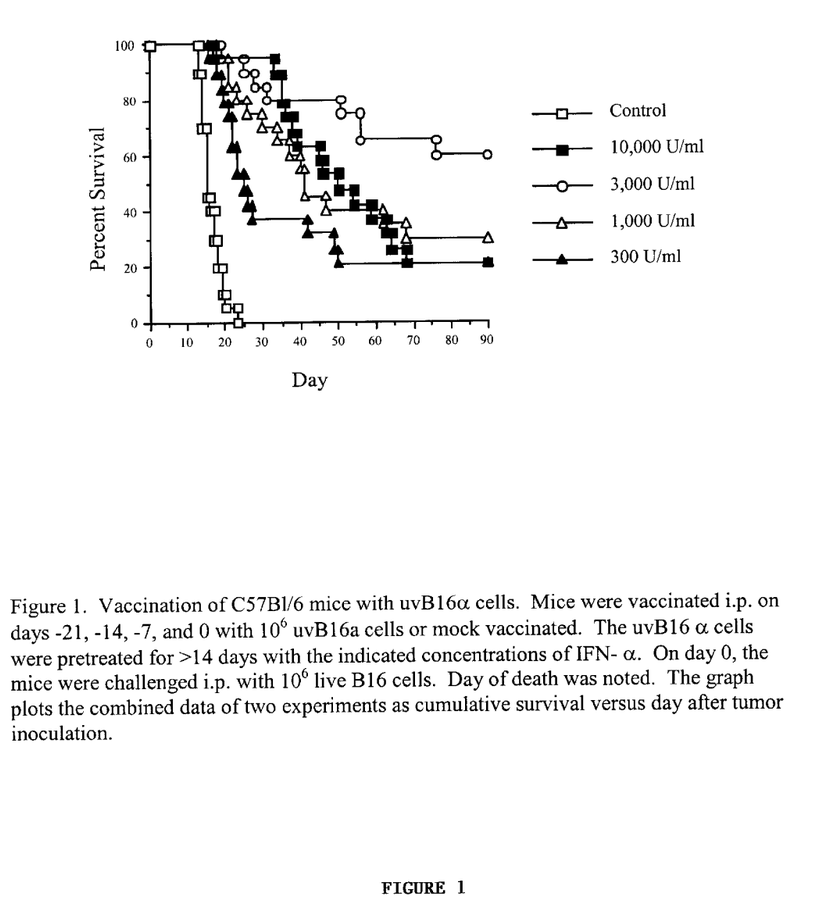
FIG. 1 depicts a graph of survival rates of mice vaccinated with UV B16-alpha cells.

Effect of in vitro IFN-α treatment concentration on vaccination potency: Our previous results suggested that UV-light inactivated B16 cells pretreated with IFN-α for more than 2 weeks (UV-B16α cells) might be useful as a vaccine against live parental tumor cells. Thus, it was important for us to determine whether there was an ideal in vitro IFN-α treatment concentration for the creation of UV-B16α cells. Therefore, B16 cells were grown for long term in the presence of various IFN-α concentrations (B16α cells). Following UV-inactivation, $10^6$ UV-B16α cells were injected, without the administration of any adjuvant, once a week for 4 weeks before challenge with $10^6$ live B16 parental cells. As shown in Table 1 and FIG. 1, the efficacy of vaccination varied, according to a complex dose-response curve, with the concentration of IFN-α to which the UV-B16α cells had been exposed. Mice vaccinated with UV-B16α cells that had been grown for long term in 10,000 U/ml, 3,000 U/ml, 1,000 U/ml, and 300 U/ml yielded survival rates of 21% (p<0.0001), 60% (p<0.0001), 30% (p<0.0001), and 21% (p<0.0001), respectively. These results suggested that the optimal concentration of IFN-α required for inducing the maximal vaccination potency of UV-B16α cells occurred at 3,000 U/ml, since vaccination with UV-B16α cells grown in both higher and lower IFN-α concentrations gave significantly less survival (3,000 U/ml vs. 300 U/ml: p=0.0016; 3,000 U/ml vs. 1,000 U/ml; p=0.043; 3,000 U/ml vs. 10,000 U/ml; p=0.021). Hereafter, all further experiments employed UV-B16α cells that were cultured long term in 3,000 U/ml of IFN-α.

TABLE 1

| Cells Vaccinated[a] | Treatment (U/ml IFN-α) | Number of Survivors (90 days) | Day of Death[b] Mean ± SE | Day of Death[b] Median | Increased Life Span |
|---|---|---|---|---|---|
| 1. None | None | 0/20 | 16.2 ± 0.6 | 15 | |
| 2. B16α | 300 | 4/19 | 26.9 ± 2.8 | 23 | 68 ± 19% |
| 3. B16α | 1,000 | 6/20 | 36.6 ± 4.0 | 36 | 125 ± 25% |
| 4. B16α | 3,000 | 12/20 | 42.8 ± 7.0 | 41 | 164 ± 47% |
| 5. B16α | 10,000 | 4/19 | 45.9 ± 3.7 | 45 | 184 ± 23% |

[a]Mice were vaccinated with uvB16α cells on days −21, −14, −7 and 0 before i.p. challenge with $10^6$ live B16 tumor cells on day 0. uvB16α cells had been treated for more than 2 weeks with the indicated concentrations of IFN-α.
[b]Survivors are excluded.
Logrank survival analysis: 1 vs. 2: p < 0.0001; 1 vs. 3: p < 0.0001; 1 vs. 4: p < 0.0001; 1 vs. 5: p < 0.0001; 4 vs. 2: p = 0.0016; 4 vs. 3: p = 0.043; 4 vs. 5: p = 0.021.
Student's t test analysis of Increased Life Span: 1 vs. 2: p = 0.0003; 1 vs. 3: p < 0.0001; 1 vs. 4: p < 0.0001; 1 vs. 5: p < 0.0001.

Figure 2:
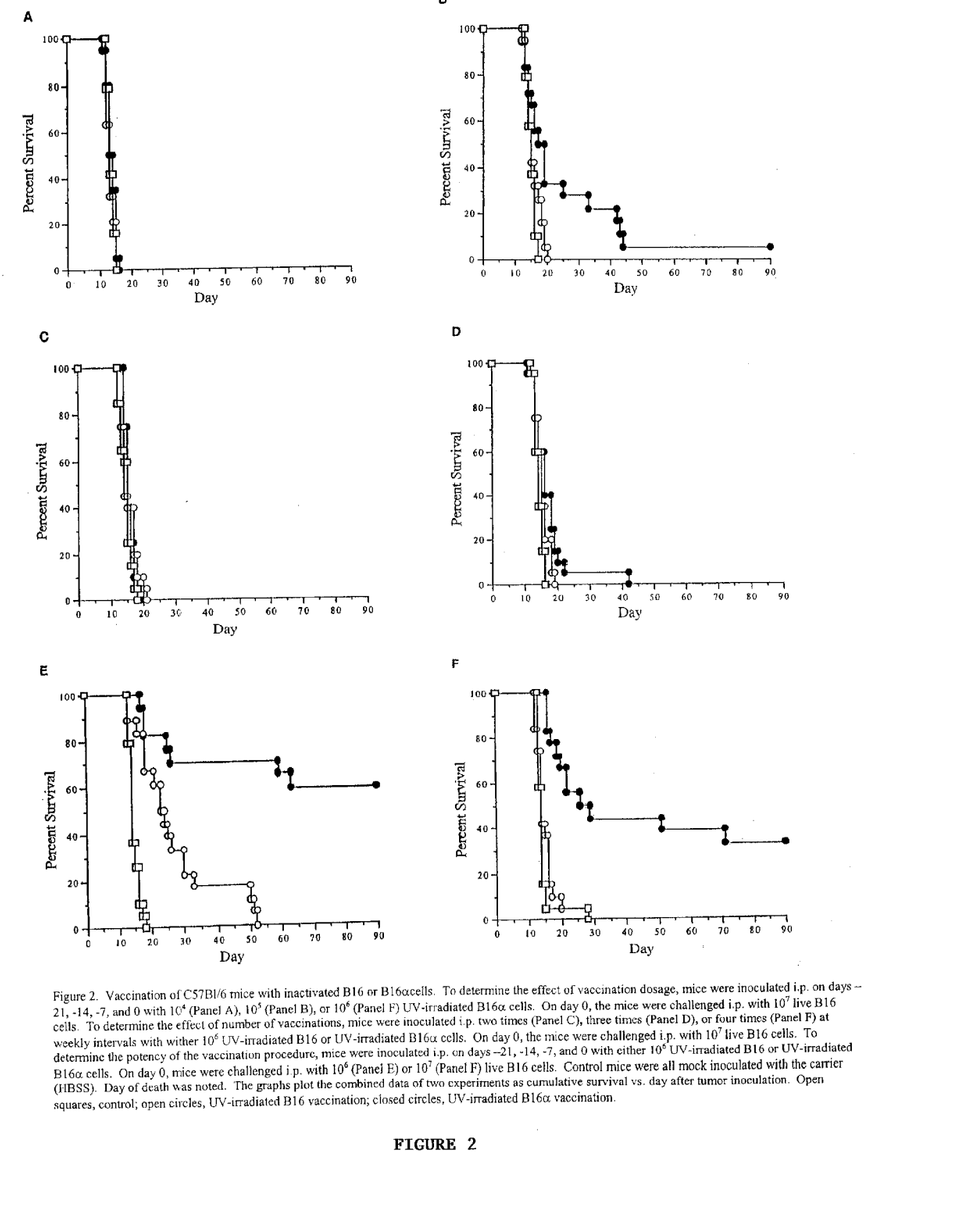
FIG. 2 depicts a graph of survival rates of mice vaccinated with inactivated B16/B16-alpha cells.

Effect of vaccination dosage on protection against live B16 parental cell challenge. The above results clearly demonstrated that there was an optimal concentration of IFN-α required to create a more effective UV-B16α cell vaccine. Equally important, the dosage effect of this vaccine had to be investigated. To test this parameter, various concentrations of UV-B16α cells were used for vaccination. Mice were vaccinated with $10^4$, $10^5$, or $10^6$ cells/0.1 ml carrier of UV-B16 or UV-B16α cells four times at weekly intervals before challenge with $10^7$ B16 cells (rather than $10^6$ B16 cells as in the experiments described above). Regardless of the vaccination dosage, vaccination of mice with UV-B16 cells did not provide any significant level of protection (Table 2 and FIGS. 2A, B, and F). In contrast, vaccination of mice with UV-B16α cells provided a substantial and significant dose-dependent level of protection against challenge with B16 cells. The increased life span increased from 2% (p=Not Significant, NS) to 45% (p=0.0057) to 90% (p=0.0013) as the vaccinating dose of UV-B16α cells rose from $10^4$ to $10^6$ cells. More strikingly, the survival rate rose from 0% to 6% (p=NS) to 33% (p=0.0080) with the vaccination dosages. The observation that only 33% of the mice survived compared to 60% in the previous experiments was presumably due to the use of a very high challenge dose in these experiments ($10^7$ versus $10^6$).

TABLE 2

| Cells Vaccinated[a] | Vaccination Dosage (Number) of Cells | Number of Survivors (90 days) | Day of Death[b] Mean ± SE | Day of Death[b] Medium | Increased Life Span |
|---|---|---|---|---|---|
| 1. None | | 0/19 | 13.4 ± 0.2 | 13 | |
| 2. B16 | $10^4$ | 0/19 | 13.2 ± 0.3 | 13 | −2 ± 2% |
| 3. B16α | $10^4$ | 0/20 | 13.6 ± 0.3 | 14 | 2 ± 2% |
| 4. None | | 0/19 | 14.8 ± 0.3 | 15 | |
| 5. B16 | $10^5$ | 0/19 | 15.5 ± 0.5 | 15 | 4 ± 3% |
| 6. B16α | $10^5$ | 1/18 | 22.0 ± 2.7 | 17 | 45 ± 16% |
| 7. None | | 0/19 | 14.4 ± 0.8 | 14 | |
| 8. B16 | $10^6$ | 0/19 | 15.3 ± 0.8 | 14 | 5 ± 5% |
| 9. B16α | $10^6$ | 6/18 | 27.1 ± 4.9 | 21 | 90 ± 29% |

[a]Mice were vaccinated with the indicated number of ultraviolet light irradiated B16α (uvB16α) or uvB16 cells on days −21, −14, −7 and 0 before i.p. challenge with $10^7$ live B16 tumor cells on day 0. uvB16α cells had been treated for more than 2 weeks with IFN-α (3,000 U/ml).
[b]Survivors were excluded.
Logrank survival analysis: 1 vs. 2: p = NS; 1 vs. 3: p = NS; 2 vs. 3: p = NS; 4 vs. 5: p = NS; 4 vs. 6: p = 0.0024; 5 vs. 6: p = 0.013; 7 vs. 8: p = NS; 7 vs. 9: p < 0.0001; 8 vs. 9: p < 0.0001.
Student's t test analysis of Increased Life Span: 1 vs. 2: p = NS; 1 vs. 3: p = NS; 2 vs. 3: p = NS; 4 vs. 5: p = NS; 4 vs. 6: p = 0.0057; 5 vs. 6: p = 0.013; 7 vs. 8: p = NS; 7 vs. 9: p < 0.0013; 8 vs. 9: p < 0.0024.

Effect of number of vaccinations on vaccination potency. Since the number of cells used for vaccination gave a dosage effect, it seemed likely that the number of vaccinations would also have a significant effect on the potency of vaccination using UV-B16α cells. To test this possibility, mice were vaccinated 2, 3, or 4 times at weekly intervals with UV-B16 or UV-B16α cells before challenge with live B16 cells. Again, vaccination of mice with UV-B16 cells did not provide any significant level of protective effect (Table 3 and FIGS. 2C, D, and F), confirming that UV-B16 cells were not themselves significantly immunogenic. In contrast, repeated inoculation of mice with UV-B16α cells provided an enhanced life span that increased from 7% (p=NS), to 23% (p=0.040), to 90% (p=0.0013) as the number of vaccinations increased from 2 to 3 to 4. Also, the survival rate (with a challenge dose of $10^7$ cells) was 33% for mice given 4 vaccinations versus 0% for mice given 3 or 2 vaccinations.

TABLE 3

| Cells Vaccinated[a] | Vaccination Times (Days) | Number of Survivors (90 days) | Day of Death[b] Mean ± SE | Day of Death[b] Median | Increased Life Span |
|---|---|---|---|---|---|
| 1. None | | 0/20 | 14.6 ± 0.4 | 15 | |
| 2. B16α | −7.0 | 0/20 | 15.6 ± 0.4 | 15 | 7 ± 2% |
| 3. None | | 0/20 | 14.0 ± 0.3 | 14 | |
| 4. B16α | −14, −7, 0 | 0/20 | 17.2 ± 1.4 | 16 | 23 ± 11% |
| 5. None | | 0/19 | 14.4 ± 0.8 | 14 | |
| 6. B16α | −21, −14, −7, 0 | 6/18 | 27.1 ± 4.9 | 21 | 90 ± 29% |

[a]Mice were vaccinated with the indicated number of uvB16α uvB16 cells on days −21, −14, −7 and 0 before i.p. challenge with $10^7$ live B16 tumor cells on day 0. uvB16α cells had been treated for more than 2 weeks with IFN-α (3,000) U/ml).
[b]Survivors are excluded.
Logrank survival analysis: 1 vs. 2: p = NS; 3 vs. 4: p = 0.023; 5 vs. 6: p < 0.0001.
Student's t test analysis of Increased Life Span: 1 vs. 2: p = NS; 3 vs. 4: p = 0.04; 5 vs. 6: p < 0.0013.

Evaluation of the potency of the vaccination procedure. Mice were vaccinated 4 times at weekly intervals with $10^6$ UV-B16 or UV-B16α cells as described previously. These mice were then challenged with two different concentrations of live B16 cells (Table 4 and FIGS. 2E and F). At challenge doses of $10^6$ and $10^7$ B16 cells, 59% (p<0.0001) and 33% (<0.0001) of mice vaccinated with UV-B16α cells survived. None of the mice vaccinated with UV-B16 cells survived at either challenge dose, confirming that vaccination with UV-B16 cells was not sufficient to induce protective immunity. Similar results were observed when increase in life span was measured, though at the lower challenge dose of $10^6$ cells some delay in death of UV-B16 cell-vaccinated mice was noted (84%, p=0.0001). No delay of death was noted at a challenge dose of $10^7$ in UV-B16 cell-vaccinated mice. In contrast, at the challenge dose of $10^7$, the increased life span of UV-B16α cell-vaccinated mice that died was still significantly (90%, p=0.0013). Taken together, the results indicated that the efficiency of the vaccination with UV-B16α cells was dependent on the number of B16 cells employed as a challenge dose, and the efficacy of vaccination with UV-B16α cells was more than 10-fold more potent than vaccination with UV-B16 cells.

TABLE 4

| Cells Vaccinated[a] | Vaccination Times (Days) | Number of Survivors (90 days) | Day of Death[b] Mean ± SE | Day of Death[b] Median | Increased Life Span |
|---|---|---|---|---|---|
| 1. None | | 0/20 | 14.6 ± 0.4 | 15 | |
| 2. B16α | −7, 0 | 0/20 | 15.6 ± 0.4 | 15 | 7 ± 2% |
| 3. None | | 0/20 | 14.0 ± 0.3 | 14 | |
| 4. B16α | −14, −7, 0 | 0/20 | 17.2 ± 1.4 | 16 | 23 ± 11% |
| 5. None | | 0/19 | 14.4 ± 0.8 | 14 | |
| 6. B16α | −21, −14, −7, 0 | 6/18 | 27.1 ± 4.9 | 21 | 90 ± 29% |

[a]Mice were vaccinated with the indicated number of uvB16α or uvB16 cells on days −21, −14, −7 and 0 before i.p. challenge with $10^7$ live B16 tumor cells on day 0. uvB16α cells had been treated for more than 2 weeks with IFN-α (3,000 U/ml).
[b]Survivors are excluded.
Logrank survival analysis: 1 vs. 2: p = NS; 3 vs. 4: p = 0.023; 5 vs. 6: p < 0.0001.
Student's t test analysis of Increased Life Span: 1 vs. 2: p = NS; 3 vs. 4: p = 0.04; 5 vs. 6: p < 0.0013.

Evaluation of the durability of the vaccination procedure: As indicated above, many UV-B16α cell-vaccinated mice survived challenge with $10^6$ B16 cells. To test the durability of the vaccination procedure, these mice were re-challenged with $10^6$ B16 cells 93 days after the initial challenge. In the absence of a booster vaccination, 30% of the mice survived the re-challenge (Table 5). This value was not significant when comparing 3/10 survivors of re-challenge of vaccinated mice with 0/10 survivors among controls in these two experiments. However, using the same protocol, a total of 69 control mice have been challenged for this study without a single survivor. Thus, we believe that this level of survival was highly significant when comparing 3/10 to 0/69 (p=0.0015). In addition, these results were in accord with previously published data using survivors of mice challenged with live B16α cells (grown in 10,000 U/ml of IFN-α) and treated with IFN-α (20% survival). Further, with a single $10^6$ UV-B16α cell booster vaccination given 3 days before re-challenge, 92% of the mice survived the re-challenge (p<0.0001). These studies suggested that the vaccination procedure led to the establishment of a durable immunity and that the durable immunity could be further enhanced by a booster delivered 3 days before re-challenge.

TABLE 5

| Vaccination group[a] | Booster | No. of survivors of first challenge (90 days) | No. of survivors of second challenge[b] (183 days) |
|---|---|---|---|
| 1 None[c] | None | 0/20 | |
| 2 None[d] | None | 0/10 | |
| 3 B16α | None | 10/20 | 3/10 |
| 4 B16α | One | 13/18 | 12/13 |

[a]C57B1/6 mice were vaccinated with $10^6$ inactivated B16α cells on days −21, −14, −7, and 0 before i.p. challenge with $10^6$ live B16 cells on day 0. The survivors of the initial challenge were given either one booster vaccination consisting of $10^6$ inactivated B16α inactivated B16α or one mock vaccination (carrier) on day 90, rechallenged with $10^6$ live B16 cells on day 93, and monitored for their survival for another 90 days. Control mice received only mock vaccinations with carrier (HBSS).
[b]Fisher exact probability test for the number of rechallenge survivors: group 2 vs. 3: p = NS; group 2 vs. 4: p < 0.0001; group 3 vs. 4: p ≤ 0.0032.
[c]Control mice for the first challenge (challenged on day 0).
[d]Control mice for the second challenge (challenged on day 93).

Effect of vaccination on metastatic tumor development: Another important question was whether i.p. vaccination could have a protective effect on the development of metastases at a distant site. B16-F10 cells, a highly metastatic variant of B16 cells that has been widely used in metastases studies, were employed. Mice were vaccinated with UV-B16α cells four times at weekly intervals and challenged by tail vein inoculation of $5 \times 10^5$ cells. Sixteen days later, the mice were sacrificed and metastases in the lungs were counted in a blinded manner. As shown in Table 6, mice vaccinated with UV-B16α cells showed a 65% decrease in the number of lung metastases (p<0.0001) relative to unvaccinated mice (Control). Contrarily, mice vaccinated with UV-B16 cells showed no significant decrease in the number of lung metastases. These results confirmed that vaccination with UV-B16 cells was relatively ineffectual. More importantly, they showed that i.p. vaccination with UV-B16α cells could cause a dramatic reduction in the number of B16-F10 lung metastases.

TABLE 6

| Cells Vaccinated[a] | Challenge Dosage (Number of Cells) | Number of Mice Evaluated | Number of Lung Metastases (16 days) | Median | % Decrease in Lung Metastases |
|---|---|---|---|---|---|
| 1. None | $5 \times 10^5$ | 20 | 151 ± 9 | 144 | |
| 2. B16 | $5 \times 10^5$ | 19 | 146 ± 10 | 144 | 3 ± 6 |
| 3. B16α | $5 \times 10^5$ | 20 | 53 ± 6 | 47 | 65 ± 4 |

[a]Mice were vaccinated with $10^6$ uvB16α (treated with 3,000 U/ml IFN-α for >2 wks) or uvB16 cells on days −21, −14, −7 and 0 before tail vein challenge with the indicated number of live B16F10 tumor cells on day 0. Student's t Test on % Decrease in Lung Metastases: 1 vs. 2: p = NS; 1 vs. 3: p < 0.0001; 2 vs. 3: p < 0.0001.

Effect of vaccination on an established tumor at a site distant from the vaccination site: All the above studies employed an i.p. vaccination before an i.p. or an i.v. challenge. An important question remained to be answered, however. Could i.p. or s.c. vaccination with UV-B16α cells have a curative effect on an established B16 tumor inoculated at a distant site? Mice were inoculated s.c. with $10^5$ B16 tumor cells. After allowing 3 days for the tumor to become established, a 3-week vaccination protocol was initiated, with vaccinations ($10^6$ UV-B16 or UV-B16α cells) given either i.p. or s.c. (contralaterally to the site of live cell inoculation) 4 days in a row in the first week and once in the subsequent weeks. As shown in Table 7, at 90 days post-B16 cell challenge, only 1/19 (5%) control mice and 2/17 (12%, p=NS) UV-B16 cell-vaccinated mice in the i.p. vaccination groups were tumor-free while 7/18 (39%, p=0.015) UV-B16α cell-vaccinated mice were tumor-free. In parallel, 1/17 (6%) control mice and 3/15 (20%, p=NS) UV-B16 cell-vaccinated mice in the s.c. vaccination groups were tumor-free while 8/15 (53%, p=0.0039) UV-B16α cell-vaccinated mice were tumor-free. These results, again, demonstrated that vaccination with UV-B16 cells was relatively ineffectual, as these cells did not offer any significant protection against an established tumor inoculated at a distant site. In contrast, vaccination with UV-B16α cells, either i.p. (intraperitoneally) or s.c. (subcutaneously), offered a significant protection of up to 53% against an established tumor inoculated at a distant site.

TABLE 7

| Cells Vaccinated[a] | Route of Vaccination | Mice with tumor/ mice challenged (90 days) | % Mice protected ± SE |
|---|---|---|---|
| 1. None | i.p. | 1/19 | 5 ± 5% |
| 2. B16α | i.p. | 7/18 | 39 ± 6% |
| 3. None | s.c. | 1/17 | 6 ± 6% |
| 4. B16α | s.c. | 8/15 | 53 ± 3% |

[a]Mice were inoculated s.c. with $10^5$ B16 parental tumor cells on days on day 0. After allowing 3 days for the tumor to become established, a 3-week vaccination protocol was initiated, with vaccinations ($10^6$ uv-B16α cells) given either i.p or s.c. (at a contralateral site) 4 days in a row in the first week and once in the subsequent weeks. Control mice received either i.p. or s.c. mock vaccinations with carrier.
Fisher Exact Probability Test for the % mice protected: 1 vs. 2: p = 0.015; 3 vs 4: p = 0.0039.

Evaluation of the vaccination protocol on other tumors of interest: The vaccination protocol was tested on other tumors and results shown in Table 8 indicate that the tests these tumors were not maximized, vaccination protected mice against the parental tumors. Since the cancer vaccine protocol is effective for different types of malignancies, it may have general applicability.

TABLE 8

| Cells Vaccinated[a] | Tumor Challenge[b] | Day of Death[c] | Ratio of Mice Without Tumor (90 days)[d] |
|---|---|---|---|
| 1. None | 4T1 | 21.8 ± 1.0 | 0/20 |
| 2. 4T1 | 4T1 | 22.7 ± 1.1 | 0/19 |
| 3. 4T1α | 4T1 | 33.9 ± 1.7 | 1/18 |
| 4. None | P388 | 24.0 ± 0.3 | 0/19 |
| 5. P388 | P388 | 25.6 ± 0.4 | 0/18 |
| 6. P388α | P388 | 32.6 ± 1.8 | 4/16 |
| 7. None | RMI | 14.0 ± 0.3 | 0/24 |
| 8. RM-1α | RMI | 20.1 ± 0.9 | 4/20 |

[a]Mice were vaccinated i.p. with $10^6$ 4T1α, P388α, or RM1α cells or carrier (controls) once a week for 4 weeks.
[b]Mice were challenged i.p. with $10^5$ 4T1 breast cancer, P388 lymphocytic leukemia, or RM1 prostate cancer cells.
[c]Day of death determinations do not include data for mice that survived. Student's t test for Day of Death: 1 vs. 3: p < 0.0001; 4 vs. 6: p < 0.0001; 7 vs. 8: p < 0.0001.
[d]Fisher exact probability test for the % mice protected: 1 vs. 3: p = NS; 4 vs. 6: p = 0.035; 7 vs. 8: p = 0.036.

Depletion of macrophages ablated the effects of a booster vaccination (11/12 survivors without depletion versus 1/12 survivors with depletion; p<0.0001), suggesting that macrophages function was required for induction of immunity, for either antigen processing or cytokine production. However, macrophage depletion at the time of tumor challenge had no effect, indicating that the required macrophage function was not a cytotoxic activity. IL-12 knock-out mice had an impaired ability to develop tumor immunity, as shown in Table 9, (4/20 survivors for knock-out mice versus 15/32 for normal mice), confirming the critical role of macrophages and suggesting that IL-12 production by the macrophages is important.

TABLE 9

| Mice | Cells Vaccinated[a] | Day of Death[b] | Ratio of Mice Without Tumor (90 days) | % Mice Protected[c] (Mean ± SE) |
| --- | --- | --- | --- | --- |
| 1. Normal | None | 16.9 ± 0.4 | 0/27 | 0% |
| 2. Normal | B16α | 33.6 ± 3.4 | 15/32 | 47% |
| 3. IL-12 KO | B16α | 24.1 ± 2.7 | 4/20 | 20% |

[a]Mice were vaccinated i.p. with uvB16α cells once a week for 4 weeks. Mice were then challenged i.p. with 10^6 parental B16 cells. Control mice received i.p. mock vaccinations with carrier (HBSS).
[b]Day of death determinations do not include data for mice that survived. Student's t test for day of death: 1 vs. 2: $p < 0.0001$; 1 vs. 3: $p = 0.0018$: 2 vs. 3: p = NS.
[c]Fisher exact probability test for the % mice protected: 1 vs. 2: $p = 0.0001$; 1 vs. 3: $p = 0.027$; 2 vs. 3: $p = 0.023$.

Depletion of cytotoxic CD8+ T cells partially ablated the effects of a booster vaccination (12/12 survivors without depletion versus 7/12 survivors with depletion; p=0.037), indicating the CD8+ T cells play an intermediate role in mediating the tumor immunity induced by vaccination. CD8+ knock-out mice also developed less tumor immunity (3/20 survivors for knock-out mice versus 12/25 for normal mice), as shown in Table 10. Thus, CD8+ T cells are an important, but not the sole, effector.

TABLE 10

| Mice | Cells Vaccinated[a] | Day of Death[b] | Ratio of Mice Without Tumor (90 days) | % Mice Protected[c] (Mean ± SE) |
| --- | --- | --- | --- | --- |
| 1. Normal | None | 17.1 ± 0.5 | 0/20 | 0% |
| 2. Normal | B16α | 34.8 ± 4.3 | 12/25 | 48% |
| 3. CD8 KO | B16α | 34.6 ± 3.2 | 3/20 | 15% |

[a]Mice were vaccinated i.p with uvB16α cells once a week for 4 weeks. Mice were then challenged i.p. with 10^6 parental B16 cells. Control mice received i.p. mock vaccinations with carrier (HBSS).
[b]Day of death determinations do not include data for mice that survived. Student's t test for day of death: 1 vs. 2: $p < 0.0001$; 1 vs. 3: $p < 0.0001$: 2 vs. 3: p = NS.
[c]Fisher exact probability test for the % mice protected: 1 vs. 2: $p = 0.002$; 1 vs. 3: p = NS; 2 vs. 3: $p = 0.0017$.

Helper CD4+ T cell knock-out mice failed to develop tumor immunity, indicating that CD4+ T cells are crucial, as shown in Table 11.

TABLE 11

| Mice | Cells Vaccinated[a] | Day of Death[b] | Ratio of Mice Without Tumor (90 days) | % Mice Protected[c] (Mean ± SE) |
| --- | --- | --- | --- | --- |
| 1. Normal | None | 16.2 ± 0.4 | 0/20 | 0% |
| 2. Normal | B16α | 24.0 ± 1.8 | 10/20 | 50% |
| 3. CD4 KO | B16α | 22.2 ± 3.4 | 0/20 | 0% |

[a]Mice were vaccinated i.p. with uvB16α cells once a week for 4 weeks. Mice were then challenged i.p. with 10^6 parental B16 cells. Control mice received i.p. mock vaccinations with carrier (HBSS).
[b]Day of death determinations do not include data for mice that survived. Student's t test for day of death: 1 vs. 2: $p < 0.0001$; 1 vs. 3: p = NS; 2 vs. 3: p = NS.
[c]Fisher exact probability test for the % mice protected: 1 vs. 2: $p = 0.0002$; 1 vs. 3: p = NS; 2 vs 3: $p = 0.0002$.

Figure 3:
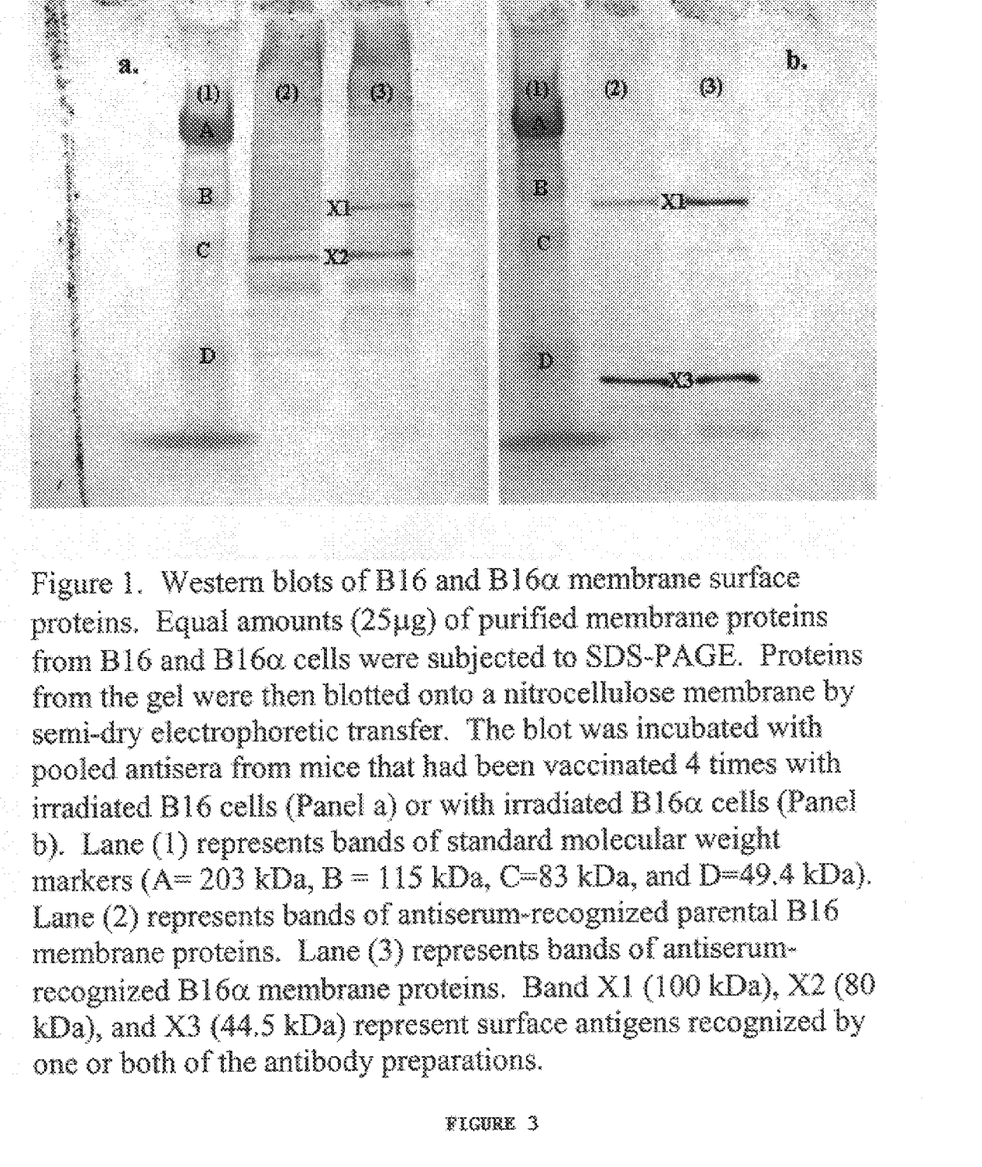
FIG. 3 is a photograph of a western blot of a gel with B16-alpha membrane proteins.

Differences in expression of surface proteins of B16 and B16α cells might trigger immunorecognition. First, retroviorus antigen expression was shown not to be involved. Next, H-2Kb (MHC class 1 antigen), ICAM-1, FAS and FAS-ligand were shown not to be involved. Others have shown that B16 melanoma cells do not express class II antigens. Western blots of PAGE gels of surface proteins from B16 and B16α cells were probed with antiserum from mice vaccinated with B16 or B16α cells. Three proteins were identified by the different antisera. The most interesting is a 44.5 kDa protein (X3; FIG. 3). Antiserum from B16α vaccinated mice recognizes the 44.5 kDa protein band in cell membrane extracts from both B16 cells and B16α cells. Antiserum from B16 vaccinated mice does not recognize this protein band. Thus, vaccination with B16α cells causes differential recognition of a specific surface protein that is not a previously recognized melanoma associated protein (gp 75 or B700).

The observation that vaccination dramatically reduces B16 metastases provide a strong rationale for treatment of human metastatic cancer. In addition, since some women have an enhanced probability of developing breast cancer, and a high proportion of men develop prostate cancer, the observation that vaccination is highly efficacious in preventing the development of B16 primary tumors may be relevant for prevention of breast and prostate cancer through prophylactic vaccination. As envisioned for human therapy, biopsies of a patient's cancer cells (or perhaps established cancer cell lines bearing appropriately matched MHC antigens) could be treated long-term with IFN-α, inactivated, and used as a vaccine to enhance the patient's immune system's ability to recognize and destroy metastatic tumors or newly developing primary tumors.

Thus, specified embodiments and applications of methods of treating diseased cells have been disclosed. It should be apparent, however, to those skilled in the art that many more modifications besides those already described are possible without departing from the invention concepts herein. For example, while most of the discussion above is directed to preventing or treating cancers, the same strategies are readily adapted to preventing or treating bacterial, viral or other infectious, infestations, cells diseased by genetic lesions (i.e., genetic defects or predispositions), by metabolic defects, or other processes. The inventive subject matter, therefore, is not to be restricted except in the spirit of the appended claims.

I claim:

1. A method of treating diseased cells in a system comprising:
   removing a sample of the diseased cells from the system;
   contacting the diseased cells with an interferon for at least 48 hours; and
   reintroducing the interferon contacted cells into the system.

2. The method of claim 1 wherein the system comprises a vertebrate animal.

3. The method of claim 2 wherein the vertebrate animal is a human.

4. The method of claim 1 wherein the diseased cells are afflicted with a disease of genetic lesion, viral, bacterial, mycotic, chemical, or structural derivation.

5. The method of claim 4 wherein the diseased cells are afflicted with a cancer.

6. The method of claim 5 wherein the cancer comprises at least one of a melanoma, a breast cancer, a liver cancer, and a prostate cancer.

7. The method of claim 1 wherein the diseased cells are infected with a bacteria.

8. The method of claim 1 wherein the diseased cells are infected with a virus.

9. The method of claim 1 wherein the interferon is a type 1 alpha interferon.

10. The method of claim 1 wherein the interferon is an alpha recombinant interferon.

11. The method of claim 1 further comprising at least partially inactivating the interferon contacted cells prior to the reintroduction.

12. The method of claim 1 wherein the step of reintroducing the interferon contacted cells comprises injecting the cells into the system subcutaneously, intraperitoneally, and intravenously.

13. The method of claim 1 wherein the step of contacting the diseased cells comprises contacting the diseased cells with an interferon for at least 36 hours.

14. The method of claim 1 wherein the step of contacting the diseased cells comprises contacting the diseased cells with an interferon for at least 48 hours.

15. The method of claim 1 wherein the step of contacting the diseased cells comprises contacting the diseased cells with an interferon for at least 72 hours.

16. The method of claim 1 wherein the step of contacting the diseased cells comprises contacting the diseased cells with an interferon for at least 5 days.

17. The method of claim 1 wherein the step of contacting the diseased cells comprises contacting the diseased cells with an interferon for at least 7 days.

18. The method of claim 1 wherein the step of contacting the diseased cells comprises contacting the diseased cells with an interferon for at least 14 days.

* * * * *